US007179615B1

(12) United States Patent
Anstey et al.

(10) Patent No.: US 7,179,615 B1
(45) Date of Patent: Feb. 20, 2007

(54) METHOD OF PROPHYLAXIS AND TREATMENT

(75) Inventors: Nicholas Mark Anstey, Jingili (AU); Joseph Brice Weinberg, Durham, NC (US); Donald L. Granger, Holladay, UT (US)

(73) Assignees: Menzies School of Health Research, Tiwi (AU); Duke University, Durham, NC (US)

( * ) Notice: Subject to any disclaimer, the term of this patent is extended or adjusted under 35 U.S.C. 154(b) by 0 days.

(21) Appl. No.: 09/124,485

(22) Filed: Jul. 29, 1998

Related U.S. Application Data

(60) Provisional application No. 60/054,114, filed on Jul. 29, 1997.

(51) Int. Cl.
*C12Q 1/18* (2006.01)
(52) U.S. Cl. .................... 435/32; 435/184; 435/189; 435/190; 435/191; 424/268.1; 424/269.1; 424/272.1; 423/405; 514/152
(58) Field of Classification Search ............... 514/152; 435/184, 190, 191, 189, 32; 424/268.1, 269.1, 424/272.1; 423/405
See application file for complete search history.

(56) References Cited

U.S. PATENT DOCUMENTS 4,895,719 A * 1/1990 Radhakrishnan et al. ..... 424/45
5,814,666 A * 9/1998 Green et al. ................. 514/611
6,153,186 A * 11/2000 Stamler et al. ........... 424/93.73

OTHER PUBLICATIONS

Seguin et al., Induction of nitric oxide synthase protects against malaria in mice exposed to irradiated *Plasmodium berghei* infected mosquitoes, Journal of Experimental Medicine 180(1):353-358 (1994).*
Liew et al., A possible novel pathway of regulation by murine T helper type 2 cells of a T helper type 1 cell activity via the modulation of the induction of nitric oxide synthase on macrophages, Eur J immunol 21(10): 2489-2494 (1991).*
Thurring et al., Lack of inducible nitric oxide synthase activity in T cell clones and T lymphocytes from native and Leishmania major infected mice, Eur J Immunol 25: 3229-3234 (1995).*
Gibaldi, What is nitric oxide and why are so many people studying it, Journal of Clinical Pharmacology, 33(6): 488-496 (1993).*
Losert et al. Experiences with severe P. falciparum malaria in the intensive care unit., Intensive Care Medicine, Feb. 2000, 26(2): 195-201 (Abstract).*
Manual of Clinical Microbiology Murray et al. eds., American Society of Microbiology (1999), p. 1355, New York.*
Cooke et al. Parasitology Today 2000 vol. 16, p. 416.*
Newbold et al. Intl. J. Parasitology 1999, vol. 29, p. 927.*
Anstey, N.M. et al., "Nitric Oxide in Tanzanian Children with Malaria: Inverse Relationship between Malaria Severity and Nitric Oxide Production/Nitric Oxide Synthase Type 2 Expression"; (1996) *J. Exp. Med.* 184:557-567.

Anstey, N.M. et al., "Nitrate levels in Malaria"; (1997) *Transactions of the Royal Soc. of Tropical Medicine and Hygiene* 91:238 (Correspondence).
Anstey, N.M. et al., "No Evidence for Increased Nitric Oxide Production in Cerebral Malaria"; *Australian Society for Infectious Diseases Annual Scientific Meeting*, Darwin, NT. May 21-24, 1995.
Anstey, N.M. et al. "No Evidence for Increased Synthesis of Nitric Oxide in Uncomplicated and Cerebral Malaria"; *Fourth International Meeting on 'Biology of Nitric Oxide ,'* Florida, USA, Sep. 17-21, 1995, (Abstract only).
Anstey, N.M. et al. "Nitric Oxide appears Protective in Tanzanian Children with Malaria: Evidence for Increased NO Production in Subclinical Infection and Suppressed Production in Clinical and Cerebral Malaria"; *The Biology of Nitric Oxide, Proceedings of the 1995 "Biology of Nitric Oxide" Conference*; S. Moncada, J. Stamler, S. Gross, E.A. Higgs, eds. p. 150 and cover pages.
Anstey, N.M. et al. "Decreased Nitrate Excretion in Tanzanian Children with Uncomplicated and Cerebral Malaria"; *44th Annual Meeting of the American Society of Tropical Medicine & Hygiene*, Texas, Nov. 1995, (Abstract only).
Bogdan, C., et al., "Lifelong Expression of Inducible NO Synthase is required for the Control of Leishmania Major Persisting in Clinically Cured Hosts"; *Fourth International Meeting on Biology of Nitric Oxide*, Florida, USA, Sep. 17-21, 1995, (Abstract only).
Clark, I.A. et al., "Nitric Oxide and Parasitic Disease", (1996) *Advances in Parasitology* 37:1-56.
Clark, I.A. et al. "Proposed Link Between Cytokines, Nitric Oxide and Human Cerebral Malaria"; (1991) *Parasitology Today* 7(8):205-207.
De Caterina, R. et al., "Nitric Oxide Decreases Cytokine-induced Endothelial Activation"; (1995) *J. Clin. Invest.* 96:60-68.
Duffy, P.E., et al. "Expression-Cloning and Immunologic Analysis of the CD36-Binding Malaria Protein, Sequestrin: Adherence Characteristics and Mechanisms of Reversal"; *44th Annual Meeting of the American Society of Tropical Medicine & Hygiene*, Texas, Nov. 1995, (Abstract only).
Kremsner, P.G. et al., "High plasma levels of nitrogen oxides are associated with severe disease and correlate with rapid paraitological and clinical cure in *Plasmodium falciparum* malaria"; (1996) *Transactions of the Royal Soc. of Tropical Medicine and Hygiene* 90:44-47.
Moncada, S. et al. "The L-Arginine-Nitric Oxide Pathway" (1993) *The New England Journal of Medicine* Dec. 30, 1993, pp. 2002-2012.

(Continued)

*Primary Examiner*—Long V. Le
*Assistant Examiner*—Jacob Cheu
(74) *Attorney, Agent, or Firm*—Greenlee, Winner and Sullivan, P.C.

(57) ABSTRACT

The present invention relates generally to a method for the prophylaxis and treatment of parasitic infections in animals and birds. More particularly, the present invention contemplates a method for the prophylaxis and treatment of *Plasmodium* infection in mammals and the prophylaxis and treatment of disease conditions caused or exacerbated by *Plasmodium*. Even more particularly, the present invention is directed to a method for the prophylaxis and treatment of malaria including ameliorating the clinical effects of malaria and agents useful for same.

4 Claims, 2 Drawing Sheets

OTHER PUBLICATIONS

Ockenhouse, C.F. et al., "Human Vascular Endothelial Cell Adhesion Receptors for *Plasmodium falciparum*-infected Erythrocytes: Roles for Endotheial Leukocyte Adhesion Molecule 1 and Vascular Cell Adhesion Molecule 1"; (1992) *The Journal of Experimental Medicine* 176:1183-1189.

Proudfoot, L. et al., "*Leishmania* Glycoconjugates Synergize with Interferon-Gamma for the Production of Nitric Oxide"; *Fourth International Meeting on 'Biology of Nitric Oxide,'* Florida, USA Sep. 17-21, 1995, (Abstract only).

Rockett, K.A. et al., "Effect of Nitric Oxide on Neuronal NMDA Channels has Implications for Human Cerebral Malaria"; *44th Annual Meeting of the American Society of Tropical Medicine Hygiene*, Texas, Nov. 1995, (Abstract only).

Schofield, L. et al., "Glycosylphosphatidylinositol Toxin of *Plasmodium* Up-Regulates Intercellular Adhesion Molecule-1, Vascular Cell Adhesion Molecule-1, and E-Selectin Expression in Vascular Endothelial Cells and Increases Leukocyte and Parasite Cytoadherence Via Tyrosine Kinase-Dependent Signal Transduction"; (1996) *The Journal of Immunology* 156:1886-1896.

Stamler, J.S. et al., "Nitric Oxide circulates in mammalian plasma primarily as an S-nitroso adduct of serum albumin"; (1992) *Proc.Natl.Acad. Sci. USA* 89:7674-7677.

Xiao, L. et al. "Cytokine Production by Endothelial Cell After Stimulation with *Plasmodiuam falciparum* Blood Stage Antigens" (Abstract only); *44th Annual Meeting of the American Society of Tropical Medicine & Hygiene*, Texas, Nov. 1995, (Abstract only).

Weinberg, J.B. et al. "Human Mononuclear Phagocyte Inducible Nitric Oxide Synthase (iNOS): Analysis of iNOS mRNA, iNOS Protein, Biopterin, and Nitric Oxide Production by Blood Monocytes and Peritoneal Macrophages"; (1995) *Blood* 86(3):1184-1195.

Yanez, D. et al. "Lymphocyte Subpopulations that Function in the Pathogenesis of Murine Cerebral Malaria"; *44th Annual Meeting of the American Society of Tropical Medicine & Hygiene*, Texas, Nov. 1995, (Abstract only).

"World Malaria Situation"; *Weekly Epidemiological Record* No. 3, Jan. 19, 1996.

* cited by examiner

METHOD OF PROPHYLAXIS AND TREATMENT

CROSS-REFERENCE TO RELATED APPLICATIONS

This application takes priority from U.S. provisional application Ser. No. 60/054,114, filed Jul. 29, 1997, which is incorporated by reference in its entirety herein.

ACKNOWLEDGMENT OF FEDERAL RESEARCH SUPPORT

This invention was made with Government support under Grant No. AR39162 awarded by the National Institutes of Health. The Government has certain rights in the invention.

The present invention relates generally to a method for the prophylaxis and treatment of parasitic infections in animals and birds. More particularly, the present invention contemplates a method for the prophylaxis and treatment of *Plasmodium* infection in mammals and the prophylaxis and treatment of disease conditions caused or exacerbated by *Plasmodium*. Even more particularly, the present invention is directed to a method for the prophylaxis and treatment of malaria including ameliorating the clinical effects of malaria and agents useful for same.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Bibliographic details of the publications numerically referred to in this specification are collected at the end of the description.

Malaria is a serious and debilitating disease caused by species of the protozoa *Plasmodium*. The organism most responsible for severe forms of malaria is *Plasmodium falciparum*. Malaria is responsible for the deaths of over 1 million people per year and severe malaria has a mortality rate of 10–30% despite the availability of a range of chemotherapeutic agents. African children are most at risk of dying from severe malaria. This form of malaria is often associated with cerebral malaria, anaemia, metabolic acidosis, hypoglycaemia and various forms of renal impairment.

The chemotherapeutic approach to the prophylaxis and treatment of malaria is hampered by the increasing development of resistance of the malaria parasite to chemotherapeutic agents. Some chemotherapeutic agents also have adverse side-effects on certain individuals or only target the parasite and not the disease condition.

The potential development of chemotherapeutic and chemoprophyl active approaches have also been hampered by non-conclusive results. This is particularly the case in relation to the effects of NO on malaria. For example, it has previously been widely reported that NO production is increased and deleterious in clinical and severe malaria and thus likely deletions in the treatment of clinical or severe malaria (21–23). However, in work leading up to the present invention, it has been determined that NO production retards parasitic growth.

There is a need to develop new therapeutic and prophylactic protocols for use alone or in conjunction with conventional chemotherapy in the prophylaxis and treatment of parasite infections and, in particular, infection by the malaria parasite.

Accordingly, one aspect of the present invention contemplates a method for the prophylaxis or treatment of infection by a protozoan parasite in an animal or bird, said method comprising administering to said animal or bird, an nitric oxide (NO) modifying agent which kills, inhibits or otherwise retards the growth, infectivity or pathogenesis of said parasite.

In a related embodiment, there is provided a method for the prophylaxis or treatment of a disease condition caused or exacerbated by a protozoan parasite in an animal or bird, said method comprising administering to said animal or bird an NO modifying agent which kills, inhibits, or otherwise retards the growth, infectivity or pathogenesis of said parasite such that the disease condition is ameliorated.

A further related embodiment of the present invention is directed to a method for the prophylaxis or treatment of infection by a protozoan parasite or a disease condition caused by a protozoan parasite in an animal or bird, said method comprising administering to said animal or bird an effective amount of an NO modifying agent for a time and under conditions sufficient to prevent or treat the infection and/or disease condition as determined by any one or more of the following parameters:

(i) inhibition, retardation or killing of any life cycle stages of said parasite;

(ii) inhibition, retardation or reduction in pathological adherence processes of parasitized host cells;

(iii) inhibition, retardation or reduction of the ability of various life cycle stages of the parasite to bind, associate or otherwise adhere to cells;

(iv) inhibition or suppression of parasite induced host production of one or more cytokines associated with pathogenesis of the disease;

(v) amelioration of clinical symptoms of the disease conditions;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

Reference herein to "nitric oxide" or "NO" encompasses all redox forms of NO including but not limited to NO⁻, NO⁻, NO⁺ and any related species. An NO modifying agent is any synthetic, recombinant or naturally occurring compound or molecule in an isolated or substantially biologically pure form which is capable of increasing or otherwise facilitating an NO effect on the parasite, the pathogenesis of the parasite or the disease condition caused by the parasite. An "NO effect" includes but is not limited to:

(i) inhibition, retardation or killing of any life cycle stages of said parasite;

(ii) inhibition, retardation or reduction in pathological adherence processes of parasitized host cells;

(iii) inhibition, retardation or reduction of the ability of various life cycle stages of the parasite to bind, associate or otherwise adhere to cells;

(iv) inhibition or suppression of parasite induced host production of one or more cytokines associated with pathogenesis of the disease;

(v) amelioration of clinical symptoms of the disease conditions;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

Examples of suitable NO modifying agents include but are not limited to (i) NO gas itself; (ii) NO donors; (iii) agents such as some cytokines, for instance growth factors and interleukins, which are capable of increasing endogenous NO levels or NO production by, for example, increasing activity or levels of NO synthase: (iv) agents which reduce NO quenching which in turn modifies removal or breakdown of NO such as superoxide dismutase; and (v) agents which modify the redox state of NO to a state which is more physiologically efficacious, such as $NO^+$. All such forms of NO modifying agents are encompassed by the term "NO modifying agent" or "NO modifying agents". In addition, an NO modifying agent may have the effect of increasing systemic NO levels or systemic NO production or increasing the availability of NO or may result in increasing localized NO levels or NO production at, for example, targeted organs, tissues, cells, parasites or parasitized cells. For example, the liver, brain, endothelial cells, macrophages/monocytes, RBCs, parasites or parasitized cells may be specifically targeted for increasing NO levels, NO production, NO availability or NO synthase. In one embodiment, for example, the brain may be targeted in the treatment of cerebral malaria. Targeting includes physical targeting, such as by syringe or catheter or biochemical targeting such as by immunological or enzyme substrate means.

The present invention is hereinafter described with reference to the protozoan organism being a *Plasmodium* species responsible or contributing to various forms of malaria. More particularly, the protozoan organism is *P. falciparum*. This is done, however, with the understanding that the present invention extends to the prophylaxis and treatment of a range of protozoan parasites other than the malaria parasite. In addition, the preferred subject to be treated is a mammal such as but not limited a human, livestock animal (eg. sheep, pig, cow, horse, donkey), companion animal (eg. cat, dog), laboratory test animal (eg. mouse, rate, guinea pig, hamster) or captive wild animal (eg. goat, fox, kangaroo, deer). Most preferably, the subject to be treated is a human.

Accordingly, a preferred aspect of the present invention provides a method for the prophylaxis or treatment of infection by a *Plasmodium* species in a mammal, said method comprising administering to said mammal an NO modifying agent which kills, inhibits or otherwise retards the growth, infectivity or pathogenesis of the *Plasmodium* species.

In a related embodiment, the present invention provides a method for the prophylaxis or treatment of a disease condition caused by or exacerbated by a *Plasmodium* species in a mammal, said method comprising administering to said mammal an NO modifying agent which kills, inhibits or otherwise retards the growth, infectivity or pathogenesis of said *Plasmodium* species such that the disease condition is ameliorated.

A further related embodiment of the present invention is directed to a method for the prophylaxis or treatment of infection by a *Plasmodium* species or a disease condition caused or exacerbated by a *Plasmodium* species in a mammal, said method comprising administering to said mammal an effective amount of an NO modifying agent for a time and under conditions sufficient to treat the infection and/or disease condition as determined by any one or more of the following parameters:

(i) inhibition, retardation or killing of any life cycle stages of said *Plasmodium* species;

(ii) inhibition, retardation or reduction in pathological adherence processes of host cells parasitized by said *Plasmodium* species;

(iii) inhibition, retardation or reduction of the ability of various life cycle stages of the *Plasmodium* species to bind, associate or otherwise adhere to cells such as but not limited to binding and invasion of hepatocytes and/or RBCs such as by sporozoites and merozoites, respectively or their equivalents.

(iv) inhibition or suppression of *Plasmodium* species induced host production of one or more cytokines associated with pathogenesis of the disease;

(v) amelioration of clinical symptoms of the disease condition;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

Preferably, the *Plasmodium* species is a malarial parasite.

Preferably, the *Plasmodium* species is *P. falciparum* or related organism.

Preferably, the mammal to be treated is a human.

A particularly preferred NO modifying agent is NO gas by inhalation having both local effects and systemic effects (see (i)–(vii) above) through transportation of NO and related species to the systemic circulation and tissues, such as but not limited to that occurring following formation of S-nitrosoproteins in the ling and pulmonary circulation.

Another preferred NO modifying agent is one capable itself of being or one resulting in the formation within the body of an NO donor of the formula R—NO, where R is an NO releasing, delivering or transferring moiety. For example, suitable R moieties include but are not limited to an amino acid, peptide, polypeptide, protein, enzyme, amine, glycolipid, polysaccharide or chemical derivatives or functional equivalents thereof. A variety of NO donors are known and reference can be conveniently made to International Patent Publication No. WO 96/02268. Accordingly, the NO modifying agents may be administered directly or NO donors formed following more convenient or less toxic administration of other NO modifying agents including but not limited to inhaled NO.

Particularly preferred NO donors are S-nitrosothiols having the formula:

$$R^1\text{—S—NO}$$

where the moiety $R^1$—S— is derived from the corresponding thiol, $R^1$—SH. The term "derived from" in relation to a corresponding thiol means that the portion represented by $R^1$—S— of the thiol is the same portion $R^1$—S— of the corresponding S-nitrosothiol, and is not intended to require that a thiol is directly converted to the corresponding S-nitrosothiol although this may be an option penicillamine, N-acetylcysteine, albumin, tissue plasminogen activator, streptokinase, a cytokine or an antagonist or agonist of a cytokine (eg. an antibody to a cytokine or soluble receptor for a cytokine or a fragment of a cytokine or a cytokine binding protein) an interferon (IFN) such as IFNα, IFNβ, IFNγ, a growth factor such as granulocyte colony-stimulating factor (G-CSF), granulocyte-macrophage colony-stimulating factor (GM-CSF), an interleukin (IL) such as IL-1 to IL-13 (IL-12 being one preferred interleukin in accordance with this aspect of the present invention), haemoglobin and a cathepsin such as cathepsin B. Particularly useful R'—S— groups are those derived from biologically acceptable thiols or thiones. Where specific targeting of an organ tissue, cell, parasite or parasitized cell is required the R, R'—S— or R'—SH group may be a substrate of, for example, an enzyme or maybe a ligand for a receptor, or an antibody to an antigen on a liver cell, brain tissue, endothelial cell, macrophage/monocyte, RBC, parasite or parasitized cell.

A particularly preferred method of delivery of RSNO to the tissues is through formation of S-nitroso proteins in the lung from inhaled NO.

The R, R'—S— or R'—SH group may include a conventional amino acid or unconventional amino acid. Non-conventional amino acids are advantageous in that they can increase stability of the NO donor during preparation and/or administration. Examples of non-conventional amino acids are shown in Table 1.

TABLE 1

| Non-conventional amino acid | Code |
| --- | --- |
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |

TABLE 1-continued

| Non-conventional amino acid | Code |
| --- | --- |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-Arginne | L-Arg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |

TABLE 1-continued

| Non-conventional amino acid | Code |
| --- | --- |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-naphthylalanine | Nmanap |
| N-methylpenicillamine | Nmpen |
| N-(p-hydroxyphenyl)glycine | Nhtyr |
| N-(thiomethyl)glycine | Ncys |
| pencillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

The NO modifying agent may be administered alone or as a dietary supplement or in combination with conventional chemotherapeutic agents and/or cytokines and/or facilitating agents. A "facilitating agent" is one which might, for example, reduce the toxicity of a NO modifying agent (eg. NO donor). For example, to reduce the toxicity of an R'—S—NO, N-acetylcysteine could be given to provide excess thiol. Alternatively, superoxide dismutase could be administered to soak up free oxygen radicals. The latter free radicals reduce NO levels and result in formation of a relatively toxic form of NO, peroxynitrite (OONO$^-$). When the NO modifying agent is administered as a dietary supplement, it would generally be other than a R'—S—NO compound. For example, it may be a substrate for conversion by NO synthase or it may be a cytokine or agonist or antagonist of a cytokine. A particularly preferred substrate for conversion by NO synthase to NO is L-arinne. Preferred cytokines according to this aspect of the present invention would, for example, promote synthesis or activity of NO synthase either directly or by interfering with cytokines which inhibit NO synthase production. Suitable cytokines for use in conjunction with the method of the present invention include those capable of inducing NO release by monocytes, such as but not limited to IL-12, δ-IFN and α-IFN.

According to a particularly preferred embodiment, the present invention is directed to a method for the prophylaxis or treatment of infection by a *Plasmodium* species in a mammal said method comprising administering to said to anal, an NO modifying agent which kills, inhibits or otherwise retards the growth, infectivity or pathogenesis of said *Plasmodium* species.

In a related embodiment, there is provided a method for the prophylaxis or treatment of malaria or another related disease condition caused or exacerbated by a *Plasmodium* species in a mammal, said method comprising administering to said mammal an NO modifying agent which kills, inhibits or otherwise retards the growth, infectivity or pathogenesis of the *Plasmodium* species such that the disease condition is ameliorated.

A further related embodiment of the present invention is directed to a method for the prophylaxis or treatment of infection by a *Plasmodium* species or a malarial disease condition caused by a *Plasmodium* species in a mammal, said method comprising administering to said mammal an effective amount of an NO modifying agent for a time and under conditions sufficient to treat the infection and/or malarial disease condition as determined by any one or more of the following parameters:

(i) inhibition, retardation or killing of any life cycle stages of said *Plasmodium* species;

(ii) inhibition, retardation or reduction in pathological adherence processes of host cells parasitized by said *Plasmodium* species;

(iii) inhibition, retardation or reduction of the ability of various life cycle stages of the *Plasmodium* species to bind, associate or otherwise adhere to cells such as but not limited to binding and invasion of hepatocytes and/or RBCs such as by sporozoites and merozoites, respectively or their equivalents.

(iv) inhibition or suppression of *Plasmodium* species induced host production of one or more cytokines associated with pathogenesis of the disease;

(v) amelioration of clinical symptoms of the disease condition;

(vi) amelioration of any ischaemia/reperfusion injury resulting from pathophysiological processes occurring in malaria or its treatment: and/or (vii) replacement of deficiency of NO at systemic, organ or tissue levels or insufficient production occurring in the disease process caused by malaria.

Preferably, the *Plasmodium* species is *P. falciparum*.

Preferably, the mammal is a human.

Reference to an "agent" is not to be taken as implying a single active molecule such as an R'—S—NO compound. Accordingly, the agent may comprise more than one compound or molecule.

The essence of this aspect of the invention is that the agent is capable of:

(i) inhibition, retardation or killing of any life cycle stages of said parasite;

(ii) inhibition, retardation or reduction in pathological adherence processes of parasitized host cells;

(iii) inhibition, retardation or reduction of the ability of various life cycle stages of the parasite to bind, associate or otherwise adhere to cells;

(iv) inhibition or suppression of parasite induced host production of one or more cytokines associated with pathogenesis of the disease;

(v) amelioration of clinical symptoms of the disease conditions;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

As far as the treatment of malaria is concerned, the agent of the present invention is capable of one or more of the following properties:

(i) inhibition, retardation or killing of any life cycle stages of said *Plasmodium* species, and in particular *P. falciparum;*

(ii) inhibition, retardation or reduction in pathological adherence processes of host cells parasitized by said *Plasmodium* species such as parasitized RBCs or parasitized hepatocytes;

(iii) inhibition, retardation or reduction of the ability of various life cycle stages of the *Plasmodium* species to bind, associate or otherwise adhere to cells such as but not limited to binding and invasion of hepatocytes and/or RBCs such as by sporozoites and merozoites, respectively of their equivalents;

(iv) inhibition or suppression of *Plasmodium* species induced host production of one or more cytokines associated with pathogenesis of the disease and in particular malaria;

(v) amelioration of clinical symptoms of the malaria;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

In one preferred embodiment, the agent is an R—NO or R'—S—NO compound alone or in combination with one or more other therapeutic molecules.

The other therapeutic agents contemplated by this aspect of the present invention may be a cytokine or a chemotherapeutic agent such as conventionally used in the prophylaxis or treatment of *Plasmodium* infection. The other therapeutic agents when used may be given simultaneously or sequentially with, for example, the R—NO or R'—S—NO compound. When given simultaneously, the agents may be in the same pharmaceutical composition or may be in separate compositions administered separately or mixed prior to administration. Separate administration includes the same or different routes of administration.

Although not intending to limit the present invention to any one theory or mode of action one of the effects of NO is to reduce or inhibit excessive cytokine production by white cells or other cell types implicated in the pathogenesis of disease caused by *Plasmodium*. Accordingly, another aspect of the present invention provides a method for inhibiting, reducing or otherwise controlling infection or disease or a risk of infection or disease of a mammal with a *Plasmodium* species, said method comprising administering to said mammal an amount of an NO modifying agent effective to reduce or inhibit excessive cytokine production by cells of the immune system which cytokines are implicated in the pathogenesis of disease caused by *Plasmodium* species.

Another effect of the NO modifying agent is an effect on the adherence of infected (parasitised) RBCs to endothelial cells as well as to other cells, such as other RBCs. In particular, it is proposed in accordance with the present invention that the NO modifying agents inhibit or reduce pathologic adherence properties of the parasites or parasitized RBCs. This inhibition may be mediated directly by NO or NO donors or by an effect on receptors such as endothelial expression of receptors. The inhibition of cytoadherence reduces the likelihood of infection or of severe infection by *Plasmodium* species.

Accordingly, another aspect of the present invention contemplates a method for inhibiting, reducing or otherwise controlling infection or disease or a risk of infection or disease of a mammal with a *Plasmodium* species, said method comprising administering to said mammal an amount of an NO modifying agent effective to reduce the pathological cytoadherence properties of the *Plasmodium* species or host cells parasitized by the *Plasmodium* species.

Preferably, the mammal is a human.

Preferably, the *Plasmodium* species is *P. falciparum*.

Pathological cytoadherence properties in this context include adherence of parasitized RBCs to endothelial cells or with other RBCs as during resetting. Cytoadherence properties also apply to the ability of various life cycle forms of the parasite to bind, associate or otherwise adhere to cells, such as invasion of hepatocytes and RBCs by sporozoites and merozoites, respectively.

In a related embodiment, the present invention is directed to a method for the prophylaxis or treatment of malaria in a human, said method comprising administering to said human an NO modifying agent comprising an NO donor in an amount effective to:

(i) increase systemic, localized or targeted NO levels;

(ii) reduce cytoadherence of parasitized RBCs to endothelial cells or other cells such as RBCs;

(iii) inhibit excess cytokine production associated with malaria severity and/or pathogenesis such as but not limited to TNFα;

(iv) reduce the clinical symptoms of malaria;

(v) amelioration of clinical symptoms of the malaria;

(vi) amelioration of any ischaemia/reperfusion injury resulting from pathophysiological processes occurring in malaria or its treatment; and/or (vii) replacement of deficiency of NO at systemic, organ or tissue levels or insufficient production occurring in the disease process caused by malaria.

The present invention, contemplates in a particularly preferred embodiment, administering an NO modifying agent in a manner that will result in increased amounts of systemic or local levels of an NO donor such as but not limited to R—NO or R'—S—NO. The administrated NO modifying agent can be but is not limited to inhaled NO, systemic administration of a cytokine or of R—NO, R—SNO or a chemical derivative or chemical equivalent thereof alone or in combination with another active compound such as but not limited to a cytokine, anti-malarial chemotherapeutic agent or an immunotherapeutic agent. The agent may be a single composition or multiple compositions administered separately via the same or different routes or mixed prior to administration.

When administered separately, the active components of the agent may be administered simultaneously or sequentially. Sequential administration includes components administered within seconds, minutes, hours or days.

The agent of this aspect of the present invention may be considered as a therapeutic agent or therapeutic composition useful in the prophylaxis or treatment of *Plasmodium* infection such as infection by *P. falciparum* in various forms of malaria.

According to this aspect of the present invention there is provided a composition for the prophylaxis or treatment of *Plasmodium* infection or of a disease condition caused or exacerbated by a *Plasmodium* species in a mammal, said composition comprising an NO modifying agent.

Preferably, the agent comprises inhaled NO, NO-inducing cytokine, an R—NO or R'—S—NO compound or other NO donor alone or in combination with another compound capable of inhibiting *Plasmodium* infection or reducing the severity of clinical symptoms associated with *Plasmodium* infection.

Preferably, the *Plasmodium* is *P. falciparum*.

The present invention further contemplates the use of an NO modifying agent in the manufacture of a medicament for the treatment of infection of a mammal or a disease condition in a manual by *Plasmodium* species.

Preferably, the *Plasmodium* species is *P. falciparum* Preferably, the mammal is a human.

Preferably, the agent is or results in the formation of an R'—S—NO compound within the circulatory system and/or tissues.

The agent useful for practising aspects of the present invention may be in any suitable form for administration. Routes of administration include but are not limited to inhalation injection (eg. IV, IM or subcutaneous injection) sublingually, intrathecally, IV drip, infusion, tablet form or rectally including in suppository form. Generally, when in composition form, the composition includes one or more pharmaceutically acceptable carriers and/or diluents. The agent may also be a genetic molecule capable of modifying NO levels molecules genetically such as by increasing production of NO synthase or modulating levels of cytokines.

In general, effective amounts of MO modulating agents and NO itself are the amounts which result in one or more of the following:

(i) increase systemic, localized or targeted NO levels;
(ii) reduce cytoadherence of parasitized RBCs to endothelial cells or other cells such as RBCs;
(iii) inhibit excess cytokine production associated with malaria severity and/or pathogenesis such as but not limited to TNFα;
(iv) reduce the clinical symptoms of malaria;
(v) amelioration of clinical symptoms of the malaria;
(vi) amelioration of any ischaemia/reperfusion injury resulting from pathophysiological processes occurring in malaria or its treatment; and/or
(vii) replacement of deficiency of NO at systemic, organ or tissue levels or insufficient production occurring in the disease process caused by malaria.

Examples of particular effective amounts are given hereunder.

When given by inhalation, it may be administered in various ways but in particular in ways which reduce the risk of toxicity. Preferably, it is administered by inhalation in a dosage of from about 0.01 to 1000 ppm, more preferably from about 500 ppm and even more preferably from about 0.1 to 100 ppm.

Agent forms suitable for injectable use include sterile aqueous solutions (where water soluble) or dispersions and sterile powders for the extemporaneous preparation of sterile injectable solutions or dispersion. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof vegetable oils, blood or RBCs or a fraction thereof, plasma or other blood product. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Other excipients generally used to stabilize the formulation may also be used.

Sterile injectable solutions are prepared by incorporating the agent in the required amount in the appropriate solvent with various of the other ingredients enumerated above, as required, followed by filtered sterilization. Generally, dispersions are prepared by incorporating the sterilized agent into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Particularly useful forms of administration include s-nitrosylation of plasma proteins and/or red cells in vivo or ex vivo and subsequent bolus or continuous infusion.

When the agent is suitably protected they may be orally administered, for example, with an inert diluent or with an assimilable edible carrier, or it may be enclosed in hard or soft shell gelatin capsule, or it may be compressed into tablets; or it may be incorporated directly with the food of the diet. For oral therapeutic administration, the agent may be incorporated with excipients and used in the form of ingestible tablets, buccal tablets, troches, capsules, elixirs, suspensions, syrups, wafers, and the like. Such compositions and preparations should contain at least 0.1% by weight of the agent and more preferably at least 1% by weight. The percentage of the compositions and preparations may, of course, be varied and may conveniently be between about 5 to about 80% of the weight of the unit. The amount of agent in such therapeutically useful compositions in such that a suitable dosage will be obtained. Preferred compositions or preparations according to the present invention are prepared so that an oral dosage unit form contains between about 0.1 μg and 2000 mg of agent. In general, effective amounts include 0.001 μg/kg body weight to 100 mg/kg body weight.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed.

In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal agent is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients. The actual amount administered can be conveniently controlled, for example during IV drip or infusion, by altering the flow rate.

The present invention extends to a diagnostic procedure where the propensity for an individual to produce effective levels of NO or NO synthase or cytokines influencing NO synthase is determined. Some chemotherapeutic and chemoprophylactic agents exhibit a certain amount of cytotoxicity or have particular adverse side effects on some subjects. These or other chemotherapeutic or chemoprophylactic agents can be very expensive. For all or some of these reasons, such chemotherapeutic or chemoprophylactic agents may not be the first treatments or prophylactics of choice for general dissemination. However, for subjects entering or living in particularly endemic areas or high risk areas, a genetic screen may first be conducted to ascertain individuals having a predisposition to produce sub-optimal levels of NO synthase or to produce a NO synthase with sub-optimal activity. These individuals, once identified, could then be the recipient of the chemotherapeutic agents listed above, with or without NO modifying agents. A genetic screen may be employed directed to polymorphisms in the NO synthase gene or NOS2 or in a regulatory region or gene capable of modulating NO synthase gene expression such as cytokines, for example α-IFN, δ-IFN, TNF, IL-1, IL-12, IL-10, IL-4 and TGF-beta. Alternatively, those individuals who were suffering from malaria may have chemotherapy, immunotherapy or treatment with an NO modifying agent based on a determination of polymorphism in, for example, a gene encoding NO synthase or a cytokine influencing NO synthase or NO production. Such a diagnostic assay, its various forms and required components are all contemplated by the present invention.

The present invention is further described by reference to the following non-limiting Figures and Examples.

The following abbreviations are used in the subject specification:

| Abbreviation | Mean |
| --- | --- |
| NO | nitric oxide or related species |
| R'-S-NO | nitrosothiol |
| SNO-cysteine | R'-S-NO where R is cysteine |
| Hb | haemoglobin |
| SNO-Hb | haemoglobin in which the thiol groups have been S-nitrosylated |
| SNO-glutathione | glutathione in which a thiol group has been S-nitrosylated |
| RBC | red blood cells |
| SNO-RBC | RBCs in which thiol groups including those on haemoglobin have been S-nitrosylated |
| IFN | interferon |
| TNF | tumour necrosis factor |
| GM-CSF | granulocyte-macrophage colony-stimulating factor |
| G-CSF | granulocyte colony-stimulating factor |
| IL | interleukin |
| HC | health control |
| AP | asymptomatic parasitemia |
| CM | clinical malaria |
| UM | uncomplicated clinical malaria |
| CM CR | clinical malaria with complete recovery |
| CM DS | clinical malaria complicated by death or neurological sequelae |
| NOS2 | nitric oxide synthase type 2 |
| $NO_x$ | nitrate + nitrite |

Examples 1 to 8 relate to a study of NO and malaria severity in children.

EXAMPLE 1

Patients

Patient subjects are conveniently assigned to a particular group. Generally, children are selected from 6 months to 9 years old. The groups are as follows: (a) healthy controls (HC), had no fever within the last 2 weeks, no parasites on thick blood film, normal white cell count and no acute illness (facture older than 1 week permitted); (b) asymptomatic parasitemia (AP) was defined as per healthy control except for the presence of *P. falciparum* parasitemia on thick blood film; (c) uncomplicated clinical malaria (CM) was defined as a febrile illness with *P. falciparum* parasitemia of ≧10,000 trophozoites/µl, no history of convulsions, no other evident cause of fever, fully alert, normal glycemic and without severe respiratory distress; (d) CM with complete recovery (CMCR) was defined as unarousable coma (2) with a Blantyre coma score (19) of ≦2 persisting for ≧30 min after the last convulsion, no other cause of coma evident from clinical or CSF analysis, any level of *P. falciparum* parasitemia on thick film examination, and recovery without neurological sequelae; and (5) CM complicated by death or neurological recovery sequelae (CMDS) was defined as for CMCR, but with coma complicated by death or neurological sequelae on discharge.

EXAMPLE 2

Dietary Control

Exogenous dietary nitrate ingestion can contribute significantly to urine and plasma nitrate levels (2, 3). A protocol using a low nitrate dinner plus an overnight fast, followed by fasting morning spot urine collections for nitrate/creatinine measurement, gives results comparable to 24-hour urine samples collected after 1–2 days of a low nitrate diet (3). The inventors, therefore, use this method of dietary control in children in the HC and AP groups.

To confirm the adequacy of the control subject's dietary nitrate restriction, the inventors place a subset of HC and AP children on a supervised standardized low nitrate diet (such as distilled water, white bread, baked chicken, and white rice cooked in distilled water) for 24 hours. Urine samples are collected after an evening meal and overnight fast as described above, as well as after a 24-hour low nitrate diet and a second overnight fast.

EXAMPLE 3

Sample Collection

Venous blood is obtained in EDTA and lithium heparin anticoagulant. Haemoglobin and white cell counts are measured using a Coulter counter. Thick blood films are stained using Field's stains A and B. Thin blood films are stained using Giemsa stain. Numbers of parasites per 200 white cells are counted from thick films. Parasitemia (per milliliter of whole blood) is then calculated from the automated white cell count. Oil immersion fields are examined by an experienced microscopist before a film is classified as negative. Urine is collected into isopropanil to prevent bacterial nitrate reduction. Plasma is aspirated from 3–4 ml of whole blood in lithium heparin anticoagulant within 30 min of collection and frozen at −70° C. Mononuclear cells are then separated by centrifugation over Ficoll/Hypaque (Lympocyte Separation medium; Organon Technica, Durham, N.C.) and stored in liquid nitrogen until use.

EXAMPLE 4

Nitrate and Nitrite Quantitation

Concentrations of nitrate and nitrite are measured by capillary electrophoresis of plasma ultrafiltrate, using a modification of the method of Leone and Kelm (4). Nitrate and nitrite concentrations are added and expressed as total $NO_x$. The final concentration of $NO_x$ is corrected for trace amounts of nitrate and nitrite in the filter units and blood collection tubes, determined by capillary electrophoresis. Plasma creatinine is measured using an Ektachem autoanalyser (Eastman Kodak Co., Rochester, N.Y.). Because 60–73% of plasma nitrate is renally excreted (5, 6), nitrate is retained and plasma $NO_x$ elevated in otherwise healthy humans with renal impairment. Plasma $NO_x$ is, therefore, corrected for renal disfunction and expressed as plasma $NO_x$/creatinine (Cr) ratio.

Urine $NO_x$ ($nNO_x$) is measured at a 1:19.3 dilution using *Pseudomonas olevoranis* nitrate reductase coupled with the Griess reaction, as described by Granger et al (7). The possibility that urine at a 1:19.3 dilution inhibits bacterial nitrate reductase is excluded by running a standard curve in the 20 CM and UM urine samples that had the lowest $NO_x$ concentrations. Because of some variability of urine concentration, spot samples are normalized, expressing nitrate concentration as a function of creatinine concentration (Sigma Diagnostics, St. Louis, Mo.). Fractional excretion of $NO_x$ ($FE_{NOx}$), the percentage of filtered $NO_x$ that is excreted, is calculated by the formula:

$$FENO_x = 100 \times (U/P\ NO_x)/(UP\ \text{creatinine}).$$

EXAMPLE 5

Cytokine Measurement

Human IL-10, TNF-α, and IL-4 are measured with commercial reagents using standard sandwich ELISAs, as described previously (8). The capture/detecting biotinylated antibody pairs used are mAb-2817508/mAb-5817503 (Medegenix, Stillwater, Minn.) for TNF, mAb-M010/mAb-011 (Endogen, Inc., Boston, Mass.) for IL-10 and polyclonal Ab-P-451/mAb-M450-B (Endogen) for IL-4. Assay sensitivities are 4.7 pg/ml for IL-10, 15.6 pg/ml for TNF, and 3.1 pg/ml for IL-4 respectively. Recombinant standards used for TNF, IL-10, and IL-4 are rhIL-10 (*Escherichia coli*)-RIL-10-5 (Endogen, rhTNF (*E. coli*)-5817510 (Medgenix), and rhIL-4 (*E. coli*)-R-IL4-5 (Endogen).

EXAMPLE 6

NOS2 Immunoblot Analysis of PBMC Extracts

Cellular extracts are prepared and analysed for NOS2 antigen content by immunoblot as previously described (9). Immunoblots are done using a monoclonal anti-NOS2 antibody (Transduction Laboratories, Lexington, Ky.; 28) and ECL reagents from Amersham (Arlington Heights, Ill.). For known negative and positive extracts, the inventors use untreated cells from the murine macrophage cell line J774 and J774 cells and cells from the human colon cell line DLD1 treated with rIIFN-γ (200 U/ml; murine for J774 cells and human for DLD1 cells) and LPS (200 ng/ml). Protein (50 μg) from the human and murine cells is used in the individual lanes. An immunoblot for NOS2 is considered positive if a clear band was visible at 130–131 kD. To quantitate NOS2 antigen, immunoblot band density is measured using a densitometer (Molecular Dynamics, Inc, Sunnyvale, Calif.).

EXAMPLE 7

Statistical Analyses

A general linear models approach (10) is used to model the relationship between markers of NO production and disease severity controlling for suspected covariates. Log transformations of the dependent variables are used to obtain normally distributed model residuals. Since there is little difference between the CMCR and CMDS groups, these groups are combined as a single CM group. Age, sex, hours since last fed, chloroquine intake, parasite count, hemoglobulin, and (in the case of plasma $NO_x$ levels and urinary $NO_x$/creatinine ratio) the plasma creatinine level, are examined for covariance. The model that included all significant parameters is considered the "best" fit. Post-hoc disease category pairwise comparisons were done using a least squares means (LSM) approach (10). For each t test, significance was evaluated using a Bonferroni adjustment for multiple comparisons (i.e. $a_{jj}$=0.05/6 =0.0083 for each $H_{jj}$; LSM [i]=LSM[j]). Pairwise comparisons of the differences between $NO_x$/creatinine ratios performed on consecutive days are performed using the Wilcoxon Rank Sum test. Differences among groups in the proportion with detectable PBMC NOS2 are assessed by chi-square followed by pairwise comparisons using Fisher's extract test (significance set at P<0.0083). The relationship between cytokine levels and disease severity is measured using the Kruskal-Wallis test followed by pairwise Mann-Whitney U tests. For this analysis, the HC and AP groups are combined. For statistical purposes, cytokine levels below the sensitivity of the assay is assigned a value of half the lower limit of detection.

EXAMPLE 8

Inverse Relationship Between Malaria Severity and Nitric Oxide Production

The purpose of this study is to compare markers of NO production [urinary and plasma nitrate+nitrite ($NO_x$)], leukocyte-inducible nitric oxide synthase type 2 (NOS2), and plasma TNF-α and IL-10 levels with disease severity in 191 Tanzanian children with and without malaria. The results are shown in Anstey et al (17). Urine $NO_x$ excretion and plasma $NO_x$ levels (corrected for renal impairment) are inversely related to disease severity, with levels highest in subclinical infection and lowest in fatal cerebral malaria. Results could not be explained by differences in dietary nitrate ingestion among the groups. Plasma levels of IL-10, a cytokine known to suppress NO synthesis, increased with disease severity. Leukocyte NOS2 antigen is detectable in all control children tested and in all those with subclinical infection, but is undetectable in all but one subject with cerebral malaria. This suppression of NO synthesis in cerebral malaria may contribute to pathogenesis. In contrast, high fasting $NO_x$ levels and leukocyte NOS2 in healthy controls and asymptomatic infection suggest that increased NO synthesis might protect against clinical disease. NO appears to have a protective rather than pathological role in African children with malaria.

EXAMPLE 9

The Effect of RSNOs on Stage Specificity

It is important to know if RSNOs have antiparastic effects against all parasite stages. Stage specificity may be an important determinant of immediate antimalarial drug efficacy in severe malaria. Examining stage specificity is also important in understanding mechanisms of effect of RSNOs, and how different stages may be affected by physiologically-occurring RSNOs. If trophozoite and schizont stage parasites are more susceptible to RSNOs than ring stages, mature parasites sequestered in the post-capillary venules may be protected from the higher concentrations of SNO-Hb found in arterial blood.

Plasmodium falciparum are cultured at 0.5–5% parasitaemia in 1% v/v oxygen, 5% v/v $CO_2$ and 94% $N_2$. The Indochina I stain is used for assays of RSNO parasite killing. Cultures are synchronised at the early ring stage (maximal age differential, 6 hours) as described (10), by sequential treatment of the parasite culture with sorbitol, followed by gelatin flotation, then a second sorbitol treatment 6 hours later. The synchronised cultures are incubated with SNO-glutathione for a 6 hour period, with drug exposure beginning at 12 hour (medium rings), 18 hour (mature rings), 24 hour (early trophozoites), 30 hour (mature trophozoites), 36 hour (early schizonts) and 42 hour (mature schizonts) after the final sorbitol synchronization. At the completion of the 6 hour incubation, Giemsa-stained thin films are made for parasite quantitation and morphological assessment, and wells harvested for measurement of tritiated hypoxanthine incorporation. Inhibition obtained at each stage of development is expressed as a percentage of the inhibition of the stage maximally affected by SNO-glutathione relative to control. The effects of different doses of SNO-glutathione are assessed.

EXAMPLE 10

Evaluation of RSNO Interaction with Antimalarial Drugs

Agents that stimulate or donate NO may have therapeutic potential in clinical and severe malaria. It is important to determine the in vitro effect on parasite killing of RSNOs in combination with commonly used antimalarial drugs. Where synergy is observed, less conventional anti-malarial agent or less NO cloner may be administered to thereby reduce potential side effects. It is also important to determine that the NO donor is not antagonistic to an antimalarial drug.

The combination of SNO-glutathione with each of the following drugs is evaluated: chloroquine (Sigma), quinine (Sigma), artemisinin and atovaquone (Wellcome Australia). Fifty percent inhibitory concentrations ($IC_{50s}$) are determined for each drug alone and for drugs in fixed combinations of their respective $IC_{50s}$(1:1, 1:3, 3:1). These data are used to construct isobolograms and to calculate fractional inhibitory concentrations (FICs) (14). The FIC is the $IC_{50}$ of one drug in the presence of the second drug, but expressed as a fraction of its $IC_{50}$ when used alone. An FIC index of <1 represents synergy or potentiation and an FIC index of >1 represents antagonism. For the chloroquine-RSNO studies, both a chloroqine-resistant and chloroquine-sensitive strain are used.

EXAMPLE 12

Effects of RSNOs on Parasite-Induced Macrophage Production of TNF-α and IL-1

The effects of RSNOs are examined on macrophage TNF and IL-1 production in response to parasite schizont extracts. Human peripheral blood mononuclear cells and the RAW 264.7 mouse macrophage cell line is used (a). Macrophages are incubated with IFN-γ and crude or partially purified schizont extracts as described. SNO-glutathione at various concentrations are added and after various incubations, cellular TNFα and IL-1 mRNA levels and/or supernatant TNF-α and IL-1 concentrations are determined quantitatively or qualitatively. The effect of multiple additions of SNO-glutathione is also determined. TNF and IL-1 production is expressed as a percentage of response to IFN-γ plus LPS. Studies are conducted by adding donor during and after cytokine treatment.

EXAMPLE 13

Effect of RSNOs on Inhibition of Pathologic Adherence Properties of Parasitised Red Cells There are several reasons why NO-related activity can be expected to inhibit cytoadherence and resetting of parasitised red blood cells (PRBC). NO is known to inhibit other physiological and pathological cytoadherence phenomena: platelet and leucocyte adherence to endothelium and platelet aggregation. Endogenous endothelial NO production and exogenous NO both selectively reduce cytokine-induced endothelial expression of adhesion molecules (13) including VCAM-1, E-selectin and to a lesser extend ICAM-1, all of which mediate cytoadherence of parasitised RBCs through binding to parasite-derived RBC ligands (14, 15). Furthermore, RSNOs may decrease binding affinity of the RBC ligand by binding to sulphydryl groups that are abundant within the cysteine rich Duffy-binding like (DBL) domains of PfEMP1, the major parasite-derived red cell protein involved in cytoadherence.

The inventors use the human microvascular endothelial cell line HMEC-1 which express inducible ICAM-1, VCAM-1 and E-selectin, and C32 melanoma cells, which express consitutive CD36 and low level ICAM-1, as controls, HMEC-1 cells more closely reflect microvascular endothelium that umbilical or saphenous vein endothelial cells.

HMEC-1 and C32 melanoma cells are grown to 50–75% confluency on glass coverslips in 24 well plates. HMEC-1 cells are incubated with 10 ng/ml interleukin-1 (IL-1) for an additional 24 hours, in order to induce VCAM-1, E-selectin and ICAM-1. Wells are also incubated with and without SNO-glutathione. Following washing and replenishment with binding medium, PRBC suspension of 10% haemoatrocrit added to all wells.

The 3D7 strain of parasites is used for cytoadherence studies. Parasites are selected with a CD36 binding phenotype by panning them over C32 melanoma cells. Parasites with a cytoadherent phenotype for HMEC-1, are selected by passing the parental 3D7 parasite strain over HMEC-1 cells. Late trophozoite/early schizont stage PRBC are incubated with the endothelial and melanoma cells for 1 hour. Following fixation and staining, the numbers of PRBC bound per 100–500 target cells will be counted. Percent binding inhibition is based on the difference between control and RSNO-treated wells.

EXAMPLE 14

Inhibition of Cytoadherence by RSNO

1) Endothelial effects of RSNO:

Initial incubation of endothelial cells with SNO-glutathione (0.2 mmol/l) is for 24 hours in conjunction with IL-1. This SNO-glutathione concentration and incubation time has previously been shown to give minimal endothelial toxicity and maximal inhibition of VCAM-1 (13). Endothelial viability is confirmed by trypan blue exclusion. Wells without SNO-glutathione is used as controls. The effects of multiple additions of lower concentrations of SNO-glutathione is also examined on subsequent cytoadherence: because of the relatively short half life of SNO-glutathione in vivo, this will more closely examine the potential physiological significance of this effect. The effect of administering SNO-glutathione prior to IL-1 is also examined.

In order to examine the mechanism of effect of SNO-glutathione on endothelial cytoadherence HMEC-1 expression of VCAM-1, E-selectin and ICAM-1 in replicate wells is quantitiated. This is performed by flow cytometry following incubation with primary and secondary antibodies as described (16).

The effect of SNO-glutathione on cytoadherence is also examined by incubating SNO-glutathione with HMEC-1 cells after IL-1 treatment. This will examine SNO-glutathione effect on cytoadherence when cytokine-induced expression of endothelial adhesion molecules has already occurred, a situation mimicking cerebral and severe falciparum malaria in humans.

In addition to the effects of exogenous RSNO, inhibition of endogenous endothelial NO production has also been shown to enhance the expression of endothelial adhesion molecules (13). The effect of inhibition of endogenous NO production is examined on cytoadherence of PBRC. HMEC-1 cells are incubated with IL-1 with or without L-N-monomethyl-arginine (L-NMMA; 1 mM), an inhibitor of NOS. This enables the inventors to look for enhanced cytoadherence of PRBC following inhibition of physiological endogenous endothelial NO production.

As a control, C32 melanoma cells are incubated with SNO-glutathione. Only the constitutively expressed molecules CD36 and to a lesser extent ICAM-1 are expressed on C32 melanoma cells. Expression of constitutively expression adhesion molecules may not be expected to be effected by RSNOs, however, CD36 is also rich in sulphydryl groups and is another potential target for RSNO mediated nitrosylation. This may decrease affinity of CD36 binding to its ligand or parasitized RBCs.

In accordance with those studies, RSNO is tested before, during and after cytokine treatments.

ii) RBC Effects of RSNO

As well as potential effects on cytoadherence through the endothelial expression of adhesion molecules, RSNO may also inhibit cytoadherence through effects on the PRBC. A plausible target is S-nitrosylation of cysteine rich domains of PfEMP1, CLAG or other parasite proteins expressed on the red cell surface which may decrease PfEMP1-endothelial binding affinity or on S-nitrosolation of proteins (including enzymes and nucleic acids) involved in their synthesis or transport. The effects of cytoadherence of RSNO treatment of PRBC is tested by adding SNO-cysteine to late trophozoite/early schizont-stage PRBC for 20 minutes just prior to the cytoadesion assay above. These SNO-PRBC are washed immediately before the 1 hour incubation with IL-1 treated HMEC-1 cells. The experiment with C32 melanoma cells is repeated to examine the effect of SNO-PRBC on cytoadherence to cells with constitutively expressed ligands.

2) Inhibition of Resetting of PRBC with Uninfected by RSNOs

The effects of RSNO administration on resetting is examined. This is the other major pathological adhesion process occurring in uncomplicated and severe malaria. Parasites are cultured as above and synchronised with sorbitol. Rosette frequency is assessed when a majority of parasites in a culture reach the pigmented trophozoite or schizont stage. Rosette frequency is assessed following addition of ethidium bromide to aliquots of a parasite culture at 5–10% parasitaemia and 1–2% haematocrit, with a wet preparation being viewed under fluorescence. Two hundred cells infected with mature parasites are counted, within the binding of two or more uninfected RBC constituting a rosette. Rosetting frequency is defined as percentage of mature-parasite-infected cells found in rosettes. Because there is strain heterogeneity in susceptibility to rosette-disrupting compounds, the effect of RSNOs is assessed on different parasite strains.

Surface and intracellular thiols of a parasite culture are S-nitrosylated with 5 mM SNO-cysteine for 20 minutes. The effects of RSNOs on rosetting is assessed in triplicate by comparing rosetting frequency with that of mock treated control cultures. The effect of different concentrations of RSNOs is also assessed.

In order to study the effects of RSNOs on the resetting properties of PRBC and RBC treated independently, the inventors purify PRBC free from uninfected erythrocytes. This involves disruption of rosettes with fucoidan followed by gelatin flotation. Purified and washed PRBC removed from the top layer readily reform rosettes when mixed with fresh red cells. Separated PRBC will be treated with SNO-cysteine as above (to make SNO-PRBC), washed then reincubated with RBC as above. Rosetting frequency with SNO-PRBC is compared with that occurring with untreated separated PRBC.

To determine if RSNO treatment of uninfected RBC reduces resetting, fresh RBC are treated with SNO-cysteine as above to produce SNO-RBC. Aliquots of untreated PRBC are reincubated with treated SNO-RBC and untreated RBC and rosetting frequency assessed.

EXAMPLE 15

Figure 1:
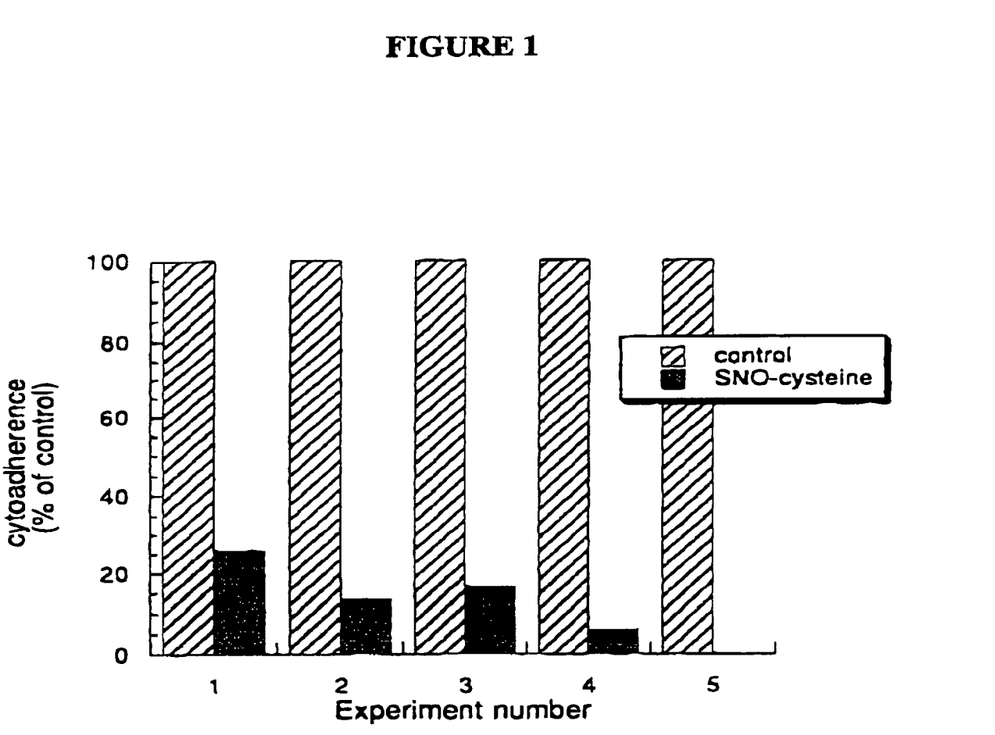
FIG. 1 is a graphical representation showing the effect of SNO-cysteine treatment of parasitised RBCs on cytoadherence to C32 melanoma cells.
Figure 2:
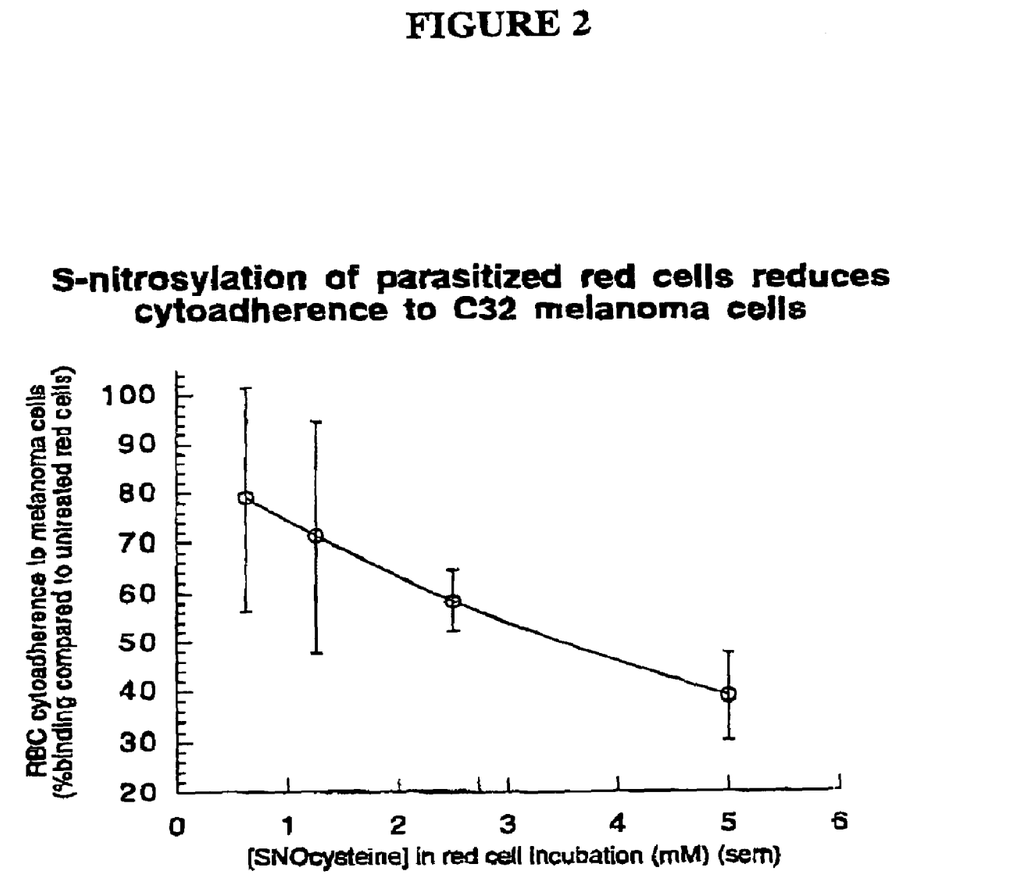
FIG. 2 is a graphical representation showing S-nitrosylation of parasitized red cells reduces cytoadherence to C32 melanoma cells.

Effect of SNO-cysteine Treatment of Parasitised RBCs Red Cells on Cytoadherence to C32 Melanoma Cells The results are shown in FIGS. 1 and 2. Five experiments were performed.

Expt 1: Treatment of parasitised red cells (*P. falicparum* JR strain) with SNO-cysteine in EDTA/phosphate buffer (final concentration 5 mM) for 10 minutes prior to incubation with C32 melanoma cells (standard C32 melanoma cell cytoadherence assay), compared with control (pretreatment for 10 minutes with same EDTA and phosphate buffer, but with only cysteine instead of SNO-cysteine).

Expt 2: Treatment and controls as per Expt 1, except that B8 strain of *P. falciparum* used and incubation of both treatment and control for 40 minutes prior to cytoadherence assay.

Expt 3: As per Expt 2, except 3D7 strain of *P. falciparum* used and that just prior to 40 minute incubation with SNO-cysteine, parasitised red cells had been resuspended in 2% w/v borate, which is known to prolong the half life of SNO-haemoglobin. The inventors use 2% w/v borate for this purpose in an RBC invasion assay.

Expt 4: As per Expt 3.

Expt 5: As per Expt 3 and 4, except that JR strain used and the control parasitised red cells bad also been resuspended in 2% w/v borate just prior to incubation with the control treatment. Thus, resuspension in borate alone did not prevent cytoadherence. Note: SNO-cysteine treatment in this experiment resulted in complete inhibition of cytoadherence (0% binding).

The data support the notion that RSNO treatment of parasitised red cells inhibits cytoadherence to C32 melanoma cells.

In an additional experiment, red cells are parasitised with *P. falciparum* strain 3D7 and then treated with SNO cysteine in EDTA/phosphate buffer (final concentration 5 mm–0.625 mM) for 40 minutes prior to incubation with C32 melanoma cells compared with control (pretreatment for 40 minutes with EDTA/phosphate buffer but with cysteine instead of SNO-cysteine.

Examples 16 to 23 relate to a study of non-immune and semi-immune adults. These examples are predicated on the proposition that NO production inversely correlates with malaria disease severity in adults.

EXAMPLE 16

Experimental Design

Clinical, parasitological, biochemical and immunological data are collected from Indonesian adults with uncomplicated and severe malaria and asymptomatic parasitaemia with fasting healthy controls. Measures of nitric oxide production (urine $NO_x$ excretion, plasma $NO_x$ concentrations and leukocyte NOS2 protein, activity and mRNA) are correlated with levels of selected Th1 and Th2 cytokines and with malaria disease severity.

EXAMPLE 17

Study Group

Adults in this study have either strictly defined severe malaria (SM) as defined by WHO or have uncomplicated clinical malaria (UM) or asymptomatic parasitaemia (AP). With a mortality rate of approximately 20% in SM, a study population of 80 SM patients enable the recruitment of approximately 16 fatal cases and 20 subjects with strictly defined cerebral malaria A sufficient number of cases of SM are selected to allow analysis of the subgroup of these cases who subsequently die. At periodic intervals during subject recruitment, the age, sex and ethnic group balance is checked between the control and disease groups to ensure no major differences occur.

The subjects are aged 16 years or older and meet the following case definitions:

a) Severe malaria (SM): as defined by WHO: asexual *P. falciparum* parasitemia (any level), and any of the following presentations (with exclusion of other diagnoses by appropriate clinical and laboratory investigations):

1) Cerebral malaria: unrousable coma persisting at least 30 mins after a generalized convulsion (Glasgow coma score $\leq 8$).
2) Severe normocytic anemia: Haemoglobin <5 g/dl in the presence of parasitemia of >10,000 µl.
3) Renal failure: urine output <400 ml/24 hrs failing to improve after rehydration, or plasma creadnine >265 umol/l.
4) Pulmonary oedema or adult respiratory distress syndrome.
5) Hypoglycaemia: whole blood glucose concentration of <2.2 mmol/l.
6) Circulatory collapse or shock: hypotension (systolic blood pressure <70 mm Hg), with cold clammy skin or core-skin temperature difference of >10° C.
7) Spontaneous bleeding: from gums, nose, gastrointestinal tract, etc. and/or substantial laboratory evidence of disseminated intravascular coagulation (DIC).
8) Repeated generalized convulsions: more than two observed within 24 hours.
9) Metabolic acidosis; arterial pH <7.25 or plasma bicarbonate <15 mmol/l.

10) Macroscopic hemoglobinuria: in a patient with normal G6PD levels.

b) Uncomplicated clinical malaria (TJM): asexual *P. falciparum* parasitemia (but not mixed), fever >38° C., compatible clinical features, no other apparent cause of fever, and no manifestations of severe disease.

c) Healthy controls (HC: healthy adults with no fever at recruitment, no fever history within last 2 weeks, no clinical evidence of infection, no diarrhea, and absence of parasites on thick film examination (100 hpf).

d) Asymptomatic parasitaemia (AP): as per HC except for presence of parasites on thick film examination.

EXAMPLE 18

Clinical Assessment

In addition to history and examination used to diagnose malaria and exclude other diagnoses, the following clinical information is gathered for patients with SM or UM, time since last intake of food (useful in excluding a confounding influence of dietary nitrate intake; time since last drink; time since admission; time since onset of coma; history of previous antimalarial ingestion; and history of convulsions. Coma score, witnessed convulsions and neurological sequelae is also documented.

EXAMPLE 19

Specimen Collection and Initial Processing

Specimens are obtained as soon as possible after subject recruitment. Venous blood is collected into $K^+$EDTA, $Na^+$ heparin and CPT mononuclear cell separation vacutainer tubes (Becton-Dickinson). Laboratory studies useful in clinical management are performed immediately: haemoglobin and white cell count, using a Coulter counter, thick and thin films for parasite quantitation, bedside blood glucose determination [using a glucometer and blood glucose sticks], renal and liver function tests [by autoanalyser]. $Na^+$ heparin plasma is frozen within 30 mins of collection at −70° C. CPT tubes are centrifuged to separate peripheral blood mononuclear cells (PBMCs), which are cryopreserved in liquid nitrogen. Whole blood blots containing parasite and human DNA are collected on filter paper.

A spot urine is collected as soon as possible after admission. Dehydrated and oliguric patients are carefully hydrated using WHO guidelines for the management of severe and complicated malaria. Because bacteria reduce nitrate to $N_2$ or $NH_3$, urine are sterilised by collection on isopropanol then frozen at −70° C. for later measurement of urinary nitrate and creatinine concentrations. Urine microscopy is performed to help exclude the unlikely event of coexistent urinary tract infection.

EXAMPLE 20

Assay Methodology

Nitrate plus nitrite ($NO_x$) determinations: Nitrate is measured by reducing nitrate to nitrite with *Aspergillus* nitrate reductase (Boehringer Mannheim). Total nitrite is then measured spectrophotometrically using the Griess reagent. Because of variability of urine concentrations, spot samples are normalised, expressing nitrate concentration as a function of creatinine concentration. Plasma $NO_x$ is measured following ultrafiltration through a Millipore Ultrafree device.

NOS2 immunoblot analysis of PBMC extracts: Cellular extract are prepared and analysed for NOS2 antigen content by immunoblot analysis. Immunoblots are done using a monoclonal anti-NOS2 antibody (Transduction Labs) and the Enhanced Chemi-luminescence ("ECL") reagents (Amersham). For known negative and positive extracts, untreated cells are used from the murine macrophage cell line J774, and J774 cells and cells from the human colon cell line DLD 1 treated with recombinant IFN-γ and LPS. An immunoblot for NOS2 is considered positive if a clear band is visible at 130–131 kD. To quantitate NOS2 antigen, immunoblot band density will be measured using a densitometer.

NOS activity: NOS activity is measured by conversion of L-arginine to L-citrulline. Briefly, cell extracts from mouse J774 cells and human PBMCs are prepared by three to five freeze-thaw cycles. Lysates are assayed for protein and NOS activity in triplicate.

Cytokine Protein: Plasma is assayed for selected Th1 (TNF, IFN-γ, IL-12) and Th2 (IL-10, TGF-β) cytokines using commercially available ELISA kits.

Whole blood paper blots and cryopreserved blood pellets and mononuclear cells are stored for quantitation of Th1 and Th2 cytokine and NOS2 mRNA and studies to determine NOS2 and cytokine gene polymorphisms associated with protection from clinical or severe malaria or a predisposition to these conditions. Similar studies are performed on such samples from the African children described in Example 1.

EXAMPLE 21

Confounding Effect of Dietary Nitrate Intake

Human nitrate excretion comprises exogenous dietary and inhaled nitrate in addition to endogenously-produced nitrate. Potential differences in dietary nitrate ingestion between the study groups may confound any differences in urinary nitrate excretion and plasma NOx levels identified. Most commonly consumed Indonesian foods appear to be low in nitrate, with low nitrate foods such as rice, noodles, leaves of vegetables, and fresh meats comprising the bulk of dietary intake. Dietary intake of most high nitrate foods [process, preserved and cured foods; wines, melons and berries] is infrequent, particularly in the lowest socioeconomic group likely to form the bulk of the study population. However, potentially high nitrate foods such as stems of vegetables are not uncommonly consumed. Nitrate containing fertilizers are not commonly used in domestic cultivation in the region. Leaching of nitrate fertilizers into the local water supply is not, therefore, considered to be a problem.

Exogenous urinary nitrate excretion falls quickly with fasting. The half life of exogenous nitrate in human volunteers commencing a nitrate-free diet is approximately 6–8 hours. In adults, severe malaria usually develops after several days of fever and anorexia. The contribution of dietary nitrate ingestion to total urinary NOx excretion in this group is thus negligible. Because anorexia is also a common symptom in adults with UM, it is also unlikely that this group will have had recent significant oral nitrate intake. Adults with UM will, however, not be recruited if they have ingested any of the following foods in the preceding 12 hours: process, preserved and cured foods; wine, melons and berries, stems of vegetables. In the HC and AP control groups, fasting plasma and urine are collected. In brief, a standardised supervised low nitrate diet (baked chicken & rice cooked in distilled water) is provided for the evening meal. Subjects are fasted overnight except for ad libitum distilled water. On the next morning the first voided urine is discarded and the second voided urine collected after a distilled water challenge.

EXAMPLE 23

Renal Impairment

Sixty to 73% of plasma $NO_x$ is renally excreted. Nitrate is retained and plasma $NO_x$ elevated in otherwise healthy adults with renal failure. Renal impairment has accounted for the elevated plasma nitrate levels reported in a number of uncontrolled studies attempting to extrapolate NO production from $NO_x$ levels in severe malaria and failure to correct for renal impairment has led to an incorrect conclusion of increased NO production in severe malaria in these reports (18, 19, 20). The $NO_x$ creatinine ratio is considered to be a valid correction for renal impairment in adults with severe malaria. Because dialysis will alter the relationship between plasma $NO_x$ and creatinine, patients who have been dialysed are excluded from the study.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. World Health Organization. 1996. World malaria situation in 1993. *Weekly Epidemiological Record* 71: 17–24.
2. Mitchell, H. H., H. A. Shonle, and H. S. Grindley. *J. Biol. Chem.* 24; 461–490, 1996.
3. Granger, D. L., W. C. Miller, and J. B. Hobbs, Jr. Methods of analyzing nitric oxide production in the immune response. In Methods in Nitric Oxide (NO) Research, M Feelisch and J. S. Stamler, editors. John Wiley & Sons, Chichester, UK. 603–618, 1996.
4. Leone, A., and M. Kelm. Appendix in Capillary electrophoretic and liquid chromatographic analysis of nitrite and nitrate. In Methods in Nitric Oxide (NO) Research. M. Feelisch and J. S. Stamler, editors. John Wiley & Sons, chichester, UK. 499–508, 1996.
5. Westfelt, U. N., G. Benthin, S. Lundin, O. Strenqcist and A. Wennmalm. *Br. J. Pharmaceol.* 114: 1621–1624, 1995.
6. Green, L. C., K. Ruiz de Luxuriaga, D. A. Wagner, W. Rand, N. Istfa, V. R. Young and S. R. Tannenbaum. *Proc. Natl. Acad. Sci. USA* 78: 7764–7768, 1981.
7. Granger, D. L., R. R. Taintor, K. S., Boockvar, and J. B. Hibbs Jr. *Methods.* 7: 78–83, 1995.
8. Harlow, E., and D. Lane. Antibodies. A Laboratory Manual. Cold Spring Harbour Laboratory Press, Cold Spring Harbour, N.Y., 1988.
9. Weinberg, J. B., M. A. Misukonis, P. J. Shami, S. N. Mason, D. L. Sauls, W. A. Dittman. E. R. Wood, G. K. Smith, B. McDonald, K. E. Bachus et al. *Blood.* 86: 1184–1195, 1995.
10. SAS/STAT User's Guide. 4th edition. SAS Institute, Cary, N.C. 846 pp, 1989.
11. Stamler, J. S., O. Jaraki, J. Osborne, D. I. Simon, J. Keaney, J. Vita, D. Singel, C. R. valeri and J. Loscalzo. *Proc. Nat. Acad. Sci. USA* 89: 16:7674–7, 1992.
12. Moncada, S., et al. *New Engl. J. Med.* 329: 2002–2012, 1993.
13. Decaterina, R. P. et al. *J. Clin. Invest.* 96: 1:60–68, 1995.
14. Berendt, A. R. et al. *Nature* 341: 57–59, 1989.
15. Ockenhouse, C. F., et al. *J. Exp. Med* 176, 4: 1183–9, 1992.
16. Schofield, L., et al, *J. of Immunol.* 156: 1886–1896, 1996.
17. Anstey, N. M. et al. *J. Exp. Med.* 184: 557–567, 1996.
18. Kremsner, P. G., et al. *Trans. R. Soc. Trop. Med. Hyg.* 90:44–47, 1996.
19. Prada, J., et al. *Parasitol Today* 11: 409–410, 1995.
20. Al Yama, F. M., et al. *Trans. R. Soc. Trop. Med. Hyg.* 90:270–273, 1996.
21. Clark, I. A. and K. A. Rocket. *Adv. Parasitol.* 37: 1–56,1996.
22. Clark, I. A. et al. *Parasitol Today* 7: 205–207, 1991.
23. Clark, I. A. et al. *Lancet* 340: 205–207, 1991.

The invention claimed is:

1. A method of inhibiting cytoadherence of parasitized cells in a subject parasitized by a *Plasmodium* species, said method comprising administering to said subject an agent for a time and under conditions sufficient to inhibit or reduce pathologic adherence properties of the parasitized cells, wherein said agent is L-arginine.

2. A method according to claim 1 wherein the agent is administered by inhalation.

3. A method according to claim 1, wherein the *Plasmodium* species is selected from the group consisting of *Plasmodium falciparum, Plasmodium vivax, Plasmodium ovale*, and *Plasmodium malariae*.

4. A method according to claim 3 wherein the *Plasmodium* species is *Plasmodium falciparum*.

* * * * *